United States Patent
Okumura et al.

(10) Patent No.: US 11,555,023 B2
(45) Date of Patent: Jan. 17, 2023

(54) PROCESS FOR THE DIFFERENTIAL SOLUBILITY-DRIVEN ASYMMETRIC TRANSFORMATION OF SUBSTITUTED 2H-CHROMENE-3-CARBOXYLIC ACIDS

(71) Applicant: AskAt Inc., Aichi (JP)

(72) Inventors: Yoshiyuki Okumura, Aichi (JP); Yukari Inami, Aichi (JP); Bas Dros, Groningen (NL); Michel Sebastiaan Leeman, Groningen (NL)

(73) Assignee: AskAt Inc., Aichi (JP)

( * ) Notice: Subject to any disclaimer, the term of this patent is extended or adjusted under 35 U.S.C. 154(b) by 4 days.

(21) Appl. No.: 17/423,280

(22) PCT Filed: Jan. 20, 2020

(86) PCT No.: PCT/JP2020/001630
§ 371 (c)(1),
(2) Date: Jul. 15, 2021

(87) PCT Pub. No.: WO2020/153279
PCT Pub. Date: Jul. 30, 2020

(65) Prior Publication Data
US 2022/0144792 A1 May 12, 2022

Related U.S. Application Data (60) Provisional application No. 62/795,156, filed on Jan. 22, 2019.

(51) Int. Cl.
*C07D 311/58* (2006.01)
(52) U.S. Cl.
CPC ................... *C07D 311/58* (2013.01)
(58) Field of Classification Search
CPC ............................ C07D 311/58; A61K 31/352
USPC .......................................... 549/405; 514/456
See application file for complete search history.

(56) References Cited

U.S. PATENT DOCUMENTS

| 6,034,256 A | 3/2000 | Carter et al. |
| 6,077,850 A | 6/2000 | Carter et al. |
| 2006/0016683 A1 | 1/2006 | Chekal et al. |
| 2006/0020022 A1 | 1/2006 | Chekal et al. |

FOREIGN PATENT DOCUMENTS

| CN | 103012350 | 4/2013 |
| JP | 2002-527512 | 8/2002 |
| JP | 2008-507501 | 3/2008 |

OTHER PUBLICATIONS

International Search Report and Written Opinion of the International Searching Authority dated Apr. 14, 2020 in International (PCT) Application No. PCT/JP2020/001630.
International Preliminary Report on Patentability dated May 3, 2021 in International (PCT) Application No. PCT/JP2020/001630.
Brands et al., "Crystallization-Induced Diastereomer Transformations", Chemical Reviews, 2006, vol. 106, No. 7, pp. 2711-2733.
Beaver et al., "Crystallization-Induced Dynamic Resolution of a Diarylmethylamine toward the Synthesis of a Potent TRPM8 Inhibitor", Organic Process Research & Development, 2016, vol. 20, pp. 1341-1346.
Yoshioka, "Racemization, Optical Resolution and Crystallization-Induced Asymmetric Transformation of Amino Acids and Pharmaceutical Intermediates", Topics in Current Chemistry, 2007, vol. 269, pp. 83-132.
Yagishita et al., "Deracemization of Axially Chiral Nicotinamides by Dynamic Salt Formation with Enantiopure Dibenzoyltartaric Acid (DBTA)", Molecules, 2013, vol. 18, pp. 14430-14447.

*Primary Examiner* — Jeffrey H Murray
(74) *Attorney, Agent, or Firm* — Wenderoth, Lind & Ponack, L.L.P.

(57) ABSTRACT

This invention relates to a method for preparing a desired isomer of a substituted 2-trifluoromethyl-2H-chromene-3-carboxylic acid, which is characterized by comprising: (a) contacting the substituted 2-trifluoromethyl-2H-chromene-3-carboxylic acid with a chiral amine to form salts, wherein the chiral amine is selected so that the solubility of the amine salt of the undesired substituted 2-trifluoromethyl-2H-chromene-3-carboxylic acid is greater than the amine salt of the desired substituted 2-trifluoromethyl-2H-chromene-3-carboxylic acid, and (b) irradiating the mixture with an ultraviolet (UV) light, wherein the irradiation increases the amount of the less soluble chiral amine salt of the substituted of the 2-trifluoromethyl-2H-chromene-3-carboxylic acid in the mixture.

8 Claims, 3 Drawing Sheets

[Fig. 1]

CpdA: substituted 2-trifluoromethyl-2H-chromene-3-carboxylic acid
CpdB: chiral amine

The asymmetric center of Chiral Amine would have a small and large group, denoted $R_S$ and $R_L$ respectively.

PROCESS FOR THE DIFFERENTIAL SOLUBILITY-DRIVEN ASYMMETRIC TRANSFORMATION OF SUBSTITUTED 2H-CHROMENE-3-CARBOXYLIC ACIDS

TECHNICAL FIELD

The present invention relates to the method of converting a mixture of the isomer of substituted 2H-chromene-3-carboxylic acid to a desired optical isomer with high enantiomeric excess and with excellent chemical yields. The present invention is typically accomplished via fractional crystallization of diastereomeric chiral amine salt followed by photo-epimerization with specific wave length of UV-light irradiation, until the mother-liquor reaches a diastereomeric salts of the racemic acids, where solids of the desired optical isomer are obtained in high optical and chemical yields. Further, the present invention preferably relates to the method of producing the desired isomer of substituted 2-trifluoromethyl-2H-chromene-3-carboxylic acid.

BACKGROUND ART

Substituted 2-trifluoromethyl-2H-chromene-3-carboxylic acids and derivatives thereof are described in U.S. Pat. No. 6,034,256 (also described in EP0977748, JP4577534, CN1196692, or KR100538258). The substituted 2-trifluoromethyl-2H-chromene-3-carboxylic acids have a chiral center at the 2-position of the 2H-chromene (2H-1-benzopyran). The ring carbon atom of the chiral center is bonded to four functional groups. Two of these four functional groups are a hydrogen atom and a trifluoromethyl ("$CF_3$") group. The other two of these four functional groups are the oxygen atom and the $sp^2$ carbon atom at the 3-position of the 2H-chromene.

The chiral substituted 2-trifluoromethyl-2H-chromene-3-carboxylic acids comprise enantiomers having either the (S)- or the (R)-configuration of the four functional groups that are bonded to the carbon atom of the chiral center. The (S)- and (R)-configurations represent the three-dimensional orientation of the four functional groups about the chiral center carbon atom. The enantiomers having either the (S)- or the (R)-configuration about the carbon atom of the chiral center bonded to the 2-trifluoromethyl group are referred to herein as (2S)- and (2R)-enantiomers, respectively. The (2S)-enantiomer is the antipode (i.e., non-superimposable mirror image) of the (2R)-enantiomer and vice versa.

Generally, the (2S)- and (2R)-enantiomers of the substituted 2-trifluoromethyl-2H-chromene-3-carboxylic acids are physically and chemically identical to each other except for how they rotate plane-polarized light and how they interact with other chiral molecules such as biological enzymes, receptors, and the like. The (2S)- and (2R)-enantiomers of the substituted 2-trifluoromethyl-2H-chromene-3-carboxylic acids are more potent inhibitors of the enzyme cyclooxygenase-2 ("COX-2") than those of the enzyme cyclooxygenase-1 ("COX-1"). These enantiomers represent a 3rd generation of "COX-2 inhibitors".

Typically for a particular compound, either the (2S)- or the (2R)-enantiomer exhibits (a) more potency for COX-2, (b) greater selectivity for COX-2-over COX-1, or (c) different metabolic profiles in liver microsome preparations. Sometimes it is the (2S)-enantiomer and other times it is the (2R)-enantiomer, depending upon the particular compound considered, that has the more potent or selective inhibitory activity or superior metabolic profile. Depending upon the potency or selectivity in inhibitory activities, metabolic profile, or other biological activities of the particular compound considered, the (2S)-enantiomer is preferred for drug development in some cases and the (2R)-enantiomer is preferred in other cases.

The substituted 2-trifluoromethyl-2H-chromene-3-carboxylic acids are synthesized as a racemic mixture because a commercially viable, direct enantioselective synthesis has not yet been devised. In order to make multi-kilogram quantities of a particular enantiomer of substituted 2-trifluoromethyl-2H-chromene-3-carboxylic acid as a therapeutic agent, a mixture of the enantiomer and its antipode possibly need to be separated by enantioselective fractional crystallization with a chiral auxiliary and/or enantioselective multicolumn chromatography over chiral stationary phase (see "Enantioselective Separation Method." {PL 1} U.S. Patent Publication Number US2006/0020022 A1) and {PL 3} U.S. Patent Publication Number US2006/0016683 A1).

The goal of these enantioselective separation methods is to ultimately produce the desired enantiomer in high (preferably >99.0%) enantiomeric excess ("e.e."). However, the maximum yield is 50% in theory, as the rest is its antipode which cannot be utilized. Thus the enantioselective separation is the economic disadvantage. In fact, enantioselective fractional crystallization of a racemic mixture of certain substituted 2-trifluoromethyl-2H-chromene-3-carboxylic acids with a chiral auxiliary has been described in Examples 66 and 67 of {PL 2} U.S. Pat. No. 6,034,256 for the purpose of preparing the corresponding (2S)-enantiomers. Although the yields (as theoretical yield) from the corresponding (2S)-carboxylic acids after multiple crystallizations and extractions were 45% and 59% respectively, the yields (as actual yields) from the corresponding racemic carboxylic acids were 23% and 29% respectively.

In case of a compound of (S)-6-chloro-7-tert-butyl-2-trifluoromethyl-2H-chromene-3-carboxylic acid of the present invention, the actual yield by using known conventional optical resolution method is approximately 20% although the ideal yield of the optical resolution is 50% at maximum.

Accordingly, there is a need for cost-effective method of efficiently obtaining enantiomers, preferably of the substituted 2-trifluoromethyl-2H-chromene-3-carboxylic acid, that produces a preferred enantiomer in high yield (e.g., >70%) and enantiomeric excess (e.g., at least 95% e.e.). The method of production of the more preferred enantiomer may include enantioselective fractional crystallization, enantioselective chromatography, and/or an optional step that converts a less preferred enantiomer to a new mixture of enantiomers and a subsequent recycle step that separates the new mixture of enantiomers, thereby producing from the less preferred enantiomer additional quantities of the more preferred enantiomer. In general, fractional crystallization can be much more economical and environmentally favorable than chromatography.

The current invention provides a new and cost effective method that converts the isomeric mixture, preferably of a substituted 2-trifluoromethyl-2H-chromene-3-carboxylic acid to the desired isomer. The method is to dynamically resolve the chiral amine salt(s), utilizing the solubility differences of the diastereomeric salts in a given solvent system, under irradiation with UV light capable of affecting epimerization (racemization). In this method generally referred to a "crystallization-induced asymmetric transformation (CIAT)", epimerization or racemization of the both isomers, i.e. enantiomers, is on-going during the resolution process. Theoretically, all of the racemates are converted into the corresponding desired enantiomers.

CITATION LIST

Patent Literature

{PL 1} U.S. Patent Publication Number US2006/0020022 A1
{PL 2} U.S. Pat. No. 6,034,256
{PL 3} U.S. Patent Publication Number US2006/0016683 A1

SUMMARY OF INVENTION

Technical Problem

The present invention provides an efficient process for the preparation of a desired optical isomer of a substituted 2-trifluoromethyl-2H-chromene-3-carboxylic acid.

The method of the present invention relates to an asymmetric transformation of enriching a desired isomer of a substituted 2-trifluoromethyl-2H-chromene-3-carboxylic acid relative to an undesired isomer by light-induced and solubility-driven asymmetric transformation.

The process described as part of the present invention can be used to manufacture of cyclooxygenase-2 (COX-2) inhibitors disclosed in U.S. Pat. No. 6,034,256, which may be useful for the treatment of COX-2 mediated disorders, such as inflammation, inflammation related disorders, pain, cancer, fever, osteoarthritis, rheumatoid arthritis, migraine, neurodegenerative diseases, cardiovascular disease, osteoporosis, asthma, lupus and psoriasis, dysmenorrhea, premature labor, gout, ankylosing spondylitis, bursitis, heat burn, sprain, and contusion, etc.

Solution to Problem

The invention provides the followings:

[1] A method for preparing a desired isomer of a substituted 2-trifluoromethyl-2H-chromene-3-carboxylic acid, which is characterized by comprising:

(a) contacting the substituted 2-trifluoromethyl-2H-chromene-3-carboxylic acid with a chiral amine to form salts, wherein the chiral amine is selected so that the solubility of the amine salt of the undesired substituted 2-trifluoromethyl-2H-chromene-3-carboxylic acid is greater than the amine salt of the desired substituted 2-trifluoromethyl-2H-chromene-3-carboxylic acid, and (b) irradiating the mixture with an ultraviolet (UV) light, wherein the irradiation increases the amount of the less soluble chiral amine salt of the substituted of the 2-trifluoromethyl-2H-chromene-3-carboxylic acid in the mixture.

[2] The method according to claim 1, the method comprising:

(a) in a solvent or mixture of solvents, contacting the substituted 2-trifluoromethyl-2H-chromene-3-carboxylic acid, with a chiral amine to form salts that is partially insoluble under selected reaction conditions in the mixture, wherein the chiral amine is selected so that the solubility of the amine salt of the undesired substituted 2-trifluoromethyl-2H-chromene-3-carboxylic acid is greater than that of the amine salt of the desired substituted 2-trifluoromethyl-2H-chromene-3-carboxylic acid under the selected conditions;

(b) irradiating the mixture with an ultraviolet (UV) light source under the selected conditions, wherein the irradiation increases the amount of the less soluble chiral amine salt of the substituted 2-trifluoromethyl-2H-chromene-3-carboxylic acid in the mixture;

(c) maintaining the irradiation for a period of time effective to increase the amount of the desired chiral amine salt of the substituted 2-trifluoromethyl-2H-chromene-3-carboxylic acid isomer;

(d) separating the desired chiral amine salt of the substituted 2-trifluoromethyl-2H-chromene-3-carboxylic acid by filtration of the precipitation; and (e) liberating the free form of the desired chiral substituted-2-trifluoromethyl-2H-chromen-3-carboxylic acid from the chiral amine salt by treatment with an acid.

[3] The method according to [1] or [2], wherein the substituted 2-trifluoromethyl-2H-chromene-3-carboxylic acid is represented by the following formula I:

[Chem.1]

wherein $R^1$ is one or more independently selected from the group consisting of hydrogen, halogen, $C_1$-$C_6$-alkyl or deutero-$C_1$-$C_6$-alkyl, $C_2$-$C_6$-alkenyl or deutero-$C_2$-$C_6$-alkenyl, $C_2$-$C_6$-alkynyl or deutero-$C_2$-$C_6$-alkynyl, $C_1$-$C_6$-alkoxy or deutero-$C_1$-$C_6$-alkoxy, $C_3$-$C_6$-cycloalkyl, $C_1$-$C_6$-alkoxy-$C_1$-$C_6$-alkyl, $C_1$-$C_6$-haloalkyl, $C_1$-$C_6$-haloalkoxy, and cyano.

[4] The method according to any one of [1] to [3], wherein the substituted 2-trifluoromethyl-2H-chromene-3-carboxylic acid is selected from the group consisting of the following compound:

6-chloro-7-tert-butyl-2-trifluoromethyl-2H-chromene-3-carboxylic acid,
6-chloro-8-methyl-2-trifluoromethyl-2H-chromene-3-carboxylic acid,
6-chloro-8-ethyl-2-trifluoromethyl-2H-chromene-3-carboxylic acid,
6-chloro-5,7-dimethyl-2-trifluoromethyl-2H-chromene-3-carboxylic acid,
6,8-dimethyl-2-trifluoromethyl-2H-chromene-3-carboxylic acid,
6,8-dichloro-2-trifluoromethyl-2H-chromene-3-carboxylic acid,
8-ethyl-6-trifluoromethoxy-2-trifluoromethyl-2H-chromene-3-carboxylic acid
6-bromo-8-methyl-2-trifluoromethyl-2H-chromene-3-carboxylic acid and
6-bromo-8-(methyl-D3)-2-trifluoromethyl-2H-chromene-3-carboxylic acid.

[5] The method according to any one of [1] to [4], wherein the substituted 2-trifluoromethyl-2H-chromene-3-carboxylic acid is 6-chloro-7-tert-butyl-2-trifluoromethyl-2H-chromene-3-carboxylic acid.

[6] The method according to any one of [1] to [5], wherein the chiral amine is selected from the group consisting of (S)-(−)-2-amino-3-phenyl-1-propanol, (R)-(+)-2-amino-3-phenyl-1-propanol, L-phenylalaninol, D-phenylalaninol, (1R,2R)-(−)-2-amino-1-phenyl-1,3-propanediol, (1S,2S)-

(+)-2-amino-1-phenyl-1,3-propanediol, (S)-(−)-N-benzyl-alpha-methylbenzylamine, (R)-(+)-N-benzyl-alpha-methylbenzylamine, (R)-(+)-1-(1-naphthyl)ethylamine, (S)-(−)-1-(1-naphthyl)ethylamine, (R)-(−)-2-pyrrolidinemethanol, (S)-(+)-2-pyrrolidinemethanol, L-phenylalaninamide, D-phenylalaninamide, (+)-cinchonine, (−)-cinchonine, (−)-cinchonidine, and (+)-cinchonidine.

[7] The method according to any one of [1] to [6], wherein the temperature of the transformation mixture is in the range of from about −30° C. to about 160° C.

[8] The method according to any one of [1] to [7], wherein the UV light irradiation is carried out by the UV light having a wavelength from about 210 nm to about 450 nm.

[9] The method according to any one of [1] to [8], wherein the UV light irradiation is carried out by the UV light having a wavelength from about 330 nm to about 390 nm.

[10] The method according to any one of [1] to [9], wherein the solubility of the salt of the undesired enantiomer is 1.2 times or more than the salt of the desired enantiomer.

[11] An asymmetric transformation method of enriching a desired isomer of a substituted 2-trifluoromethyl-2H-chromene-3-carboxylic acid, which is characterized by comprising:
(a) contacting the substituted 2-trifluoromethyl-2H-chromene-3-carboxylic acid with a chiral amine to form salts, wherein the chiral amine is selected so that the solubility of the amine salt of the undesired substituted 2-trifluoromethyl-2H-chromene-3-carboxylic acid is greater than the amine salt of the desired substituted 2-trifluoromethyl-2H-chromene-3-carboxylic acid, and
(b) irradiating the transformation mixture with an ultraviolet (UV) light, wherein the irradiation increases the amount of the less soluble chiral amine salt of the substituted of the 2-trifluoromethyl-2H-chromene-3-carboxylic acid in the transformation mixture.

[12] The method according to [11], the method comprising:
(a) in a solvent or mixture of solvents, contacting the substituted 2-trifluoromethyl-2H-chromene-3-carboxylic acid, with a chiral amine to form salts that is partially insoluble under selected reaction conditions in a transformation mixture, wherein the chiral amine is selected so that the solubility of the amine salt of the undesired substituted 2-trifluoromethyl-2H-chromene-3-carboxylic acid is greater than that of the amine salt of the desired substituted 2-trifluoromethyl-2H-chromene-3-carboxylic acid under the selected conditions;
(b) irradiating the transformation mixture with an ultraviolet (UV) light source under the selected conditions, wherein the irradiating increases the amount of the less soluble chiral amine salt of the substituted 2-trifluoromethyl-2H-chromene-3-carboxylic acid in the transformation mixture;
(c) maintaining the irradiation for a period of time effective to increase the amount of the desired chiral amine salt of the substituted 2-trifluoromethyl-2H-chromene-3-carboxylic acid isomer;
(d) separating the desired chiral amine salt of the substituted 2-trifluoromethyl-2H-chromene-3-carboxylic acid by filtration of the precipitation; and
(e) liberating the free form of the desired chiral substituted-2-trifluoromethyl-2H-chromen-3-carboxylic acid from the chiral amine salt by treatment with an acid.

[13] The method according to [11] or [12], wherein the substituted 2-trifluoromethyl-2H-chromene-3-carboxylic acid is represented by the following formula I:

[Chem.2]

wherein $R^1$ is one or more independently selected from the group consisting of halogen, $C_1$-$C_6$-alkyl or deutero-$C_1$-$C_6$-alkyl, $C_2$-$C_6$-alkenyl or deutero-$C_2$-$C_6$-alkenyl, $C_2$-$C_6$-alkynyl or deutero-$C_2$-$C_6$-alkynyl, $C_1$-$C_6$-alkoxy or deutero-$C_1$-$C_6$-alkoxy, $C_3$-$C_6$-cycloalkyl, $C_1$-$C_6$-alkoxy-$C_1$-$C_6$-alkyl, $C_1$-$C_6$-haloalkyl, $C_1$-$C_6$-haloalkoxy, and cyano.

[14] The method according to any one of [11] to [13], wherein the substituted 2-trifluoromethyl-2H-chromene-3-carboxylic acid is selected from the group consisting of the following compound:
6-chloro-7-tert-butyl-2-trifluoromethyl-2H-chromene-3-carboxylic acid,
6-chloro-8-methyl-2-trifluoromethyl-2H-chromene-3-carboxylic acid,
6-chloro-8-ethyl-2-trifluoromethyl-2H-chromene-3-carboxylic acid,
6-chloro-5,7-dimethyl-2-trifluoromethyl-2H-chromene-3-carboxylic acid,
6,8-dimethyl-2-trifluoromethyl-2H-chromene-3-carboxylic acid,
6,8-dichloro-2-trifluoromethyl-2H-chromene-3-carboxylic acid,
8-ethyl-6-trifluoromethoxy-2-trifluoromethyl-2H-chromene-3-carboxylic acid
6-bromo-8-methyl-2-trifluoromethyl-2H-chromene-3-carboxylic acid and
6-bromo-8-(methyl-D3)-2-trifluoromethyl-2H-chromene-3-carboxylic acid.

[15] The method according to any one of [11] to [14], wherein the substituted 2-trifluoromethyl-2H-chromene-3-carboxylic acid is 6-chloro-7-tert-butyl-2-trifluoromethyl-2H-chromene-3-carboxylic acid.

[16] The method according to any one of [11] to [15], wherein the chiral amine is selected from the group consisting of (S)-(−)-2-amino-3-phenyl-1-propanol, (R)-(+)-2-amino-3-phenyl-1-propanol, L-phenylalaninol, D-phenylalaninol, (1R,2R)-(−)-2-amino-1-phenyl-1,3-propanediol, (1S,2S)-(+)-2-amino-1-phenyl-1,3-propanediol, (S)-(−)-N-benzyl-alpha-methylbenzylamine, (R)-(+)-N-benzyl-alpha-methylbenzylamine, (R)-(+)-1-(1-naphthyl)ethylamine, (S)-(−)-1-(1-naphthyl)ethylamine, (R)-(−)-2-pyrrolidinemethanol, (S)-(+)-2-pyrrolidinemethanol, L-phenylalaninamide, D-phenylalaninamide, (+)-cinchonine, (−)-cinchonine, (−)-cinchonidine, and (+)-cinchonidine.

[17] The method according to any one of [11] to [16], wherein the temperature of the transformation mixture is in the range of from about −30° C. to about 160° C.

[18] The method according to any one of [11] to [17], wherein the UV light irradiation is carried out by the UV light having a wavelength from about 210 nm to about 450 nm.

[19] The method according to any one of [11] to [18], wherein the UV light irradiation is carried out by the UV light having a wavelength from about 330 nm to about 390 nm.

[20] The method according to any one of [11] to [19], wherein the solubility of the salt of the undesired enantiomer is 1.2 times or more than the salt of the desired enantiomer.

DESCRIPTION OF EMBODIMENTS

The present invention does not employ optical resolution, but provides a method for preparing an optically active carboxylic acid from its racemate with high yield and high optical purity by utilizing the solubility difference in the diastereomeric salts of the racemic carboxylic acid and an optically active amine under UV light irradiation capable of affecting epimerization. Further, using the other enantiomer of the optically active amine instead, it makes possible to prepare the other enantiomer of the carboxylic acid. The preferable feature of the present method is that a single optically active substance can be obtained from a racemate with a high yield of 80% or more. This makes sharp contrast with a known conventional optical resolution in which the upper limit of the yield is 50% or less.

Enantiomers are stereoisomers with non-superimposable mirror images. Enantiomers are equal in all their chemical and physical properties in an achiral environment except for their optical rotation, as they rotate the plane of polarized light by equal amounts in opposite directions. In contrast, diastereomers are characteristically different in their chemical and physical properties, such as melting and boiling points, densities, solubilities, heats of formation, and Gibbs free energies.

In our method, racemic carboxylic acid is converted to the pair of diastereomeric salts with an optically pure amine. The two salts formed are therefore not enantiomers of each other anymore, but diastereomers. The differences of the solubility among the diastereomeric salts is utilized to prepare the optically active substance. The chiral salt obtained by our method can be decomposed to afford the free carboxylic acid by treatment with a suitably strong acid, that is, an acid stronger than that which is being converted. The decomposition of the salt generally employs a mineral acid, such as hydrochloric acid (HCl, sulfuric acid ($H_2SO_4$), phosphoric acid ($H_3PO_4$), hydrobromic acid (HBr), perchloric acid ($HClO_4$), p-toluenesulfonic acid (TsOH), methanesulfonic acid (MsOH or $CH_3SO_3H$), trifluoromethanesulfonic acid ($CF_3SO_3H$), etc. according to a conventional manner.

Thus, the present method can be applied to any carboxylic acids of racemate represented by the formula I which is known to be photo-isomerized. We explain as follows with using the theoretical background and examples of several racemate.

Photo-Isomerization of 2H-1-Benzopyran Derivative

Photo-isomerization is the conversion of a compound from one isomer to another by the action of light wherein the formation of a photo-isomer is carried out. Photochromic reaction of 2H-1-benzopyran (2H-chromene) is known in the art (e.g. J. Am. Chem. Soc., 1966, 88 (24), pp 5931-5933 and J. Phys. Chem., 1967, 71 (12), pp 4045-4048) as summarized as below. That is, the benzopyran ring is opened by UV-irradiation ($hv_1$) to give the corresponding dienone intermediate and the dienone is ring-closed to give the benzopyran ring by visible light irradiation ($hv_2$) or heating (Δ) as described in Scheme 1. Thus, the two steps, a ring-opening and a subsequent ring closure, are necessary for the photo-isomerization of the benzopyrans.

Scheme 1: Photochromic reaction of benzopyran.

[Chem.3]

Our photo-isomerization, i.e. photo-racemization of substituted 2H-chromene-3-carboxylic acid of the present invention, is considered to proceed in the same mechanism as shown in Scheme 2. The dienone intermediate in Scheme 2 well explains the loss of chirality at C-2 center. The subsequent ring closure results in the formation of the racemate, as the ring-closure step is not stereoselective. However, the dienone intermediate has not been isolated, or detected during the course of the current investigation. The ring-closure step is likely to occur much faster than the ring-opening step in this class of structures. This mechanism applies to the preparation of (RS)-form racemate from (S)- or (R)-isomer.

Scheme 2: photo-racemization of substituted 2H-chromene-3-carboxylic acid.

[Chem.4]

(R)-form (RS)-form racemate

Diastereomeric Resolution and Its Asymmetric Transformation

Figure 1:
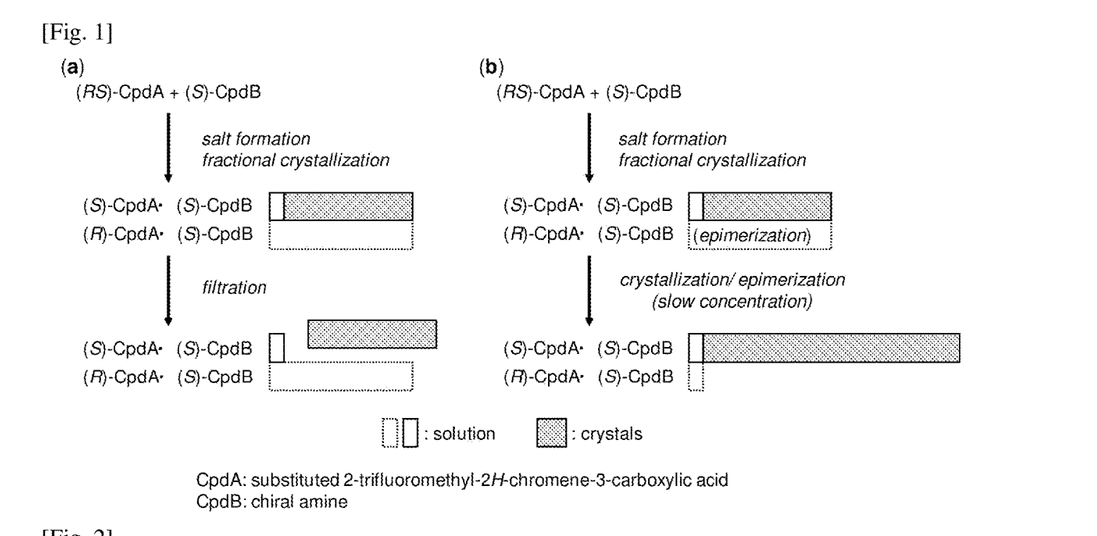
FIG. 1 shows the schematic illustration of ordinal diastereomeric resolution (a) and asymmetric transformation of the present invention (b).

The principle behind optical resolution by ordinary diastereomeric formation, as shown in FIG. 1 as disclosed in Top Curr Chem (2007) 269: 83-132, is that when a racemate ((RS)-CpdA) is reacted with a resolving agent (e.g. (S)-CpdB) in a solvent, the diastereomeric pair of (R)- and (S)-CpdA.(S)-CpdB occur and then the least soluble diastereomer (e.g. (S)-CpdA.(S)-CpdB) is separated by fractional crystallization from the resolution solution (FIG. 1(a)). In this case, the maximum yield of the desired ((S)-CpdA) is theoretically only half of the corresponding racemate ((RS)-CpdA).

On the other hand, asymmetric transformation of diastereomers of the present invention, as shown in FIG. 1(b), is characterized by that when (RS)-CpdA is reacted with a resolving agent (S)-CpdB in solution under epimerizing conditions, fractional crystallization of the less soluble (S)-CpdA.(S)-CpdB and the epimerization of the more soluble (R)-CpdA.(S)-CpdB in the solution proceed simultaneously and the diastereomeric composition of the mixture that asymmetric transformation of diastereomers consequently is greatly shifted to the crystalline (S)-CpdA.(S)-CpdB as a whole. In addition, when the solvent is gradually removed during the reaction, it results in a more favorable yield. In the present case, almost all of (RS)-CpdA.(S)-CpdB can be theoretically transformed into the desired crystalline (S)-CpdA.(S)-CpdB.

Crystallization-Induced Diastereomer Transformations (CIDT) i.e. Dynamic Crystallization of a Diastereomeric Mixture Involving Epimerization Crystallization-Induced Asymmetric Transformation (CIAT), which is used in the present invention is the combined two methodologies of 1) dynamic stereoisomerization and 2) preferential crystallization (as summarized in FIG. 2), as disclosed in Advances in Organic Crystal Chemistry Comprehensive Reviews 2015 and Chemical Reviews, 2006, 106 (7), 2711. This is a practical methodology dynamically converging on a single stereoisomeric form from a mixture of stereoisomers by simultaneous crystallization and stereoisomerization in the system.

Figure 2:
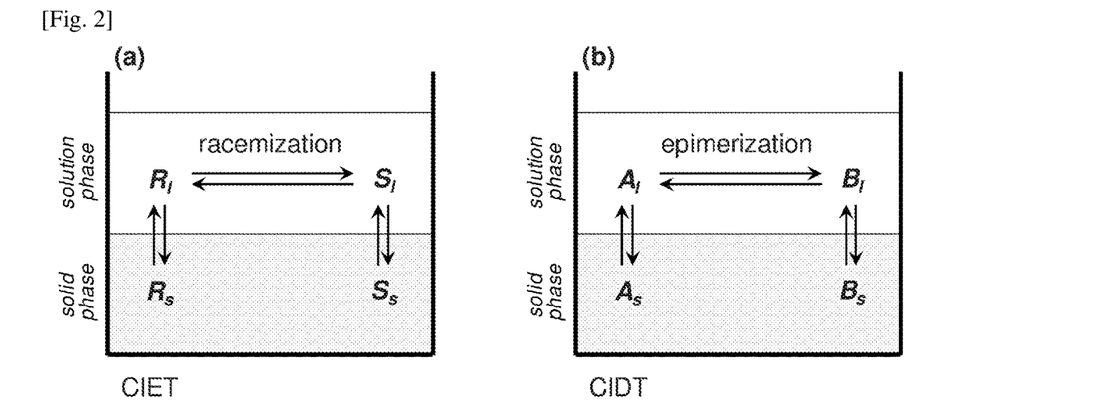
FIG. 2 shows the schematic illustration of crystallization-induced asymmetric transformation (CIAT). (a) Crystallization-Induced Enantiomer Transformation (CIET), R and S are enantiomers. (b) Crystallization-Induced Diastereomer Transformation (CIDT), A and B are diastereomers.

CIAT can be classified into two categories: one is Crystallization-Induced Enantiomer Transformation (CIET), which can resolve each enantiomer from the racemates by dynamic crystallization (FIG. 2(a)), and the other is Crystallization-Induced Diastereomer Transformation (CIDT), which is the dynamic crystallization of a diastereomeric mixture involving epimerization (FIG. 2(b)).

Figure 3:
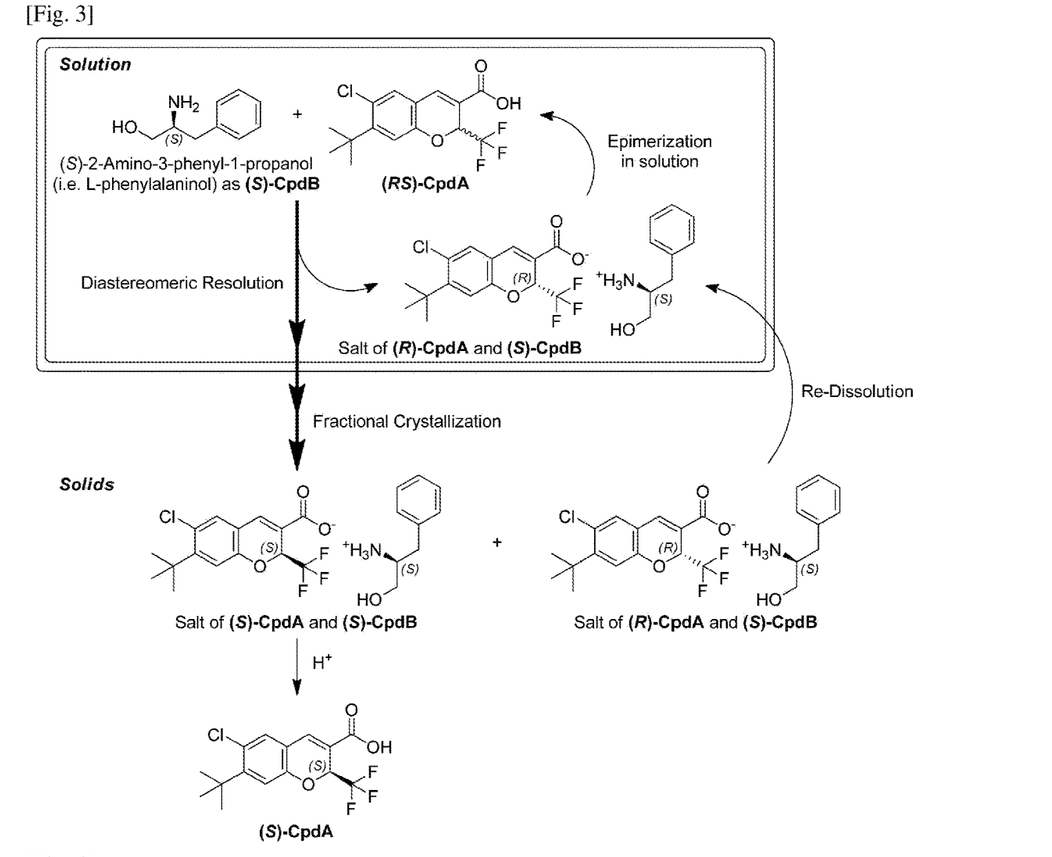
FIG. 3 shows the schematic illustration of crystallization-induced asymmetric transformation.

Further, the preferable method of the present invention is illustrated as FIG. 3.

Characteristic of the Invention

The present invention allows the practical preparation of chiral substituted 2-trifluoromethyl-2H-chromene-3-carboxylic acids in high enantiomeric excess and high yield. The process involves the conversion of racemic substituted 2-trifluoromethyl-2H-chromene-3-carboxylic acids to enantiomerically enriched or enantiomerically pure chiral substituted 2-trifluoromethyl-2H-chromene-3-carboxylic acids. The products obtained from this process can be useful intermediates for the production of active pharmaceutical ingredients (API) as well as the API itself. The process is simple and does not require covalent attachment of the chiral group (chiral auxiliary), and can be executed preferably by using a one pot conversion. Additionally, the products are obtained in high yield (e.g., >70%, preferably >80%, more preferably >90%, particular preferably >95%) and high enantiomeric excess (e.g., >95% e.e., preferably >96% e.e., more preferably >97% e.e., particular preferably >98% e.e.). Moreover, the process is economical because of a one pot process with minimal chemical usage. The process can be carried to a high degree of completion, by utilizing the racemic carboxylic acid. The chiral amine auxiliary is recovered from the resulting acidic aqueous solution, when the salt is decomposed to re-generate the target chiral carboxylic acid. Thereby the current invention minimizes cost and reduces waste.

The transformation of racemate of substituted 2-trifluoromethyl-2H-chromene-3-carboxylic acids to one desired isomer of substituted 2-trifluoromethyl-2H-chromene-3-carboxylic acids in higher enantiomeric purity begins with a pair of diastereomeric salts (2S- and 2R-) of a racemic substituted 2-trifluoromethyl-2H-chromene-3-carboxylic acid and a chiral amine. See FIG. 4.

Figure 4:
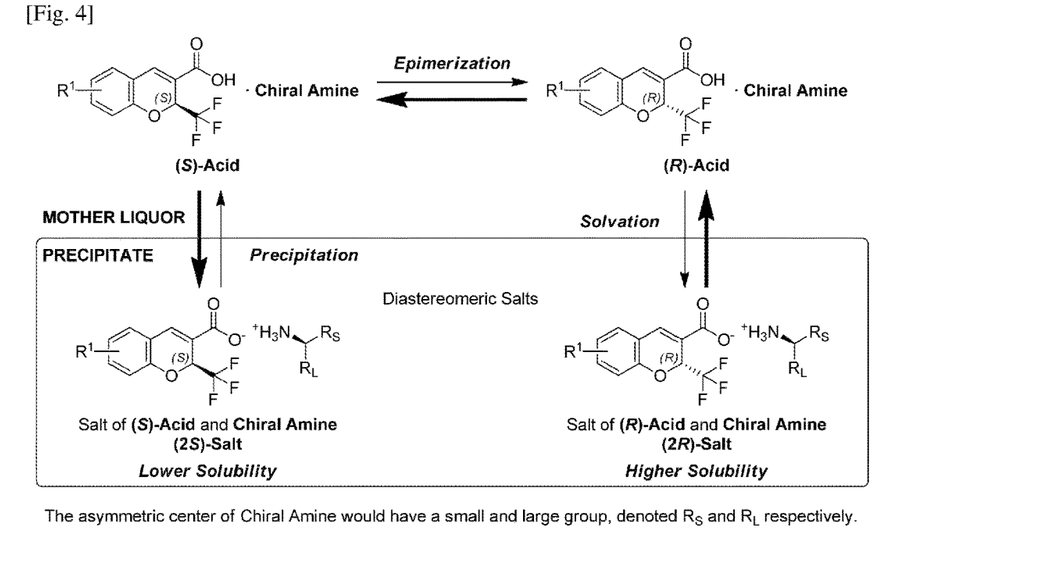
FIG. 4 shows the schematic illustration of asymmetric transformation of enriching a desired isomer of a substituted 2-trifluoromethyl-2H-chromene-3-carboxylic acid.

The substituents denoted in FIG. 4 as "$R_L$ and $R_S$" are respectively a larger group and a smaller group. The whole materials, i.e. racemic carboxylic acid and chiral amine as resolving reagent are first dissolved in a solvent completely typically at the temperature from about 10° C. to about 160° C., preferably, from about 10° C. to about 120° C., more preferably, from about 20° C. to about 85° C. When precipitation of salt solids completes after cooling the mixture of the above materials and solvent typically at the temperature from about −10° C. to about 50° C., preferably, from about −5° C. to about 45° C., more preferably, from about 0° C. to about 40° C., the epimerization process is carried out as a slurry under UV light irradiation with stirring at an appropriate temperature (e.g., about −10° C. to about 160° C., preferably about −10° C. to about 100° C., more preferably, about 0° C. to about 80° C., particular preferably about 0° C. to about 50° C.) whereby the desired isomer ((2S)-Salt in the example shown in FIG. 4) is less soluble than the undesired isomer (2R)-Salt in the solvent system of the process.

The process of the current invention is flexible and is expected to be applicable to a wide range of compounds where diastereomeric salts are least soluble compared to the corresponding acid or chiral amine, and show some degree of solubility differences between the pair of diastereomeric salts in a given solvent. The current invention also demonstrates that slow addition of the chiral amine to the racemic acid in a given solvent under UV-irradiation at room temperature, successfully converts a mixture of the diastereomeric salts to the salt of the desired single enantiomer with a high chemical yield.

Because of the differential solubilities of the diastereomeric salts, the precipitate is enriched in the desired diastereomer (2S)-Salt while the supernatant is enriched in the undesired diastereomer (2R)-Salt. The solubility of the amine salt of the desired enantiomer is typically 1.2 times or more, preferably, 2 times or more, more preferably, 3 times or more than the amine salt of the undesired enantiomer. The degree of enrichment can be relatively small, with the process still providing a useful degree of isomeric enrichment. In the supernatant the epimerization of the substituted 2-trifluoromethyl-2H-chromene-3-carboxylic acid proceeds by UV light irradiation, and the composition gradually approaches to a mixture of equal parts of (S)-Acid and (R)-Acid. This photo-epimerization results in the conversion of the more soluble diastereomer (2R)-Salt into the less soluble diastereomer (2S)-Salt. Precipitation of the excess desired diastereomer (2S)-Salt and re-solvation of the diminished undesired diastereomer (2R)-Salt occurs until a thermodynamic equilibrium mixture of diastereomers is achieved. In this way, a racemic substituted 2-trifluoromethyl-2H-chromene-3-carboxylic acid is converted into a diastereomerically enriched or pure diastereomeric salt in a single reaction vessel. The pure chiral or enantiomerically enriched substituted 2-trifluoromethyl-2H-chromene-3-carboxylic acid can be liberated from the salt by bringing the salt into contact with an acid, preferably, a strong acid such as mineral acid, which is exemplified by HCl, $H_2SO_4$, $H_3PO_4$, HBr, $HClO_4$, TsOH, $CH_3SO_3H$, $CF_3SO_3H$, etc. and the chiral amine recovered for re-use. The product of this process can then be used in other synthetic transformations. The product of the process is sufficiently enantiomerically enriched so that the product or a product from subsequent synthetic steps can be crystallized to further improve the enantiomeric excess.

Feature of UV-Light Irradiation

Typically, the present photo-epimerization method is carried out at a temperature of from about −30° C. to about 200° C. The temperature of the reaction mixture may rise during the photo-epimerization step due to heat transferred from the UV light source(s). The temperature of the reaction mixture typically is not critical. Optionally the photo-epimerization step is carried out at from −30° C. to room temperature or above. The room temperature is usually 10 to 45° C. Typically, the reaction temperature ranges from about −30° C. to about 150° C., about 0° C. to about 100° C., from about 5° C. to about 100° C., from about 15° C. to about 100° C., from about 25° C. to about 100° C., from about 35° C. to about 100° C., from about 40° C. to about 100° C., from about 50° C. to about 100° C., or from about 60° C. to about 100° C.

In addition, UV light is a spectrum of light having a wavelength of from about 210 nm to about 450 nm, preferably, from about 250 nm to 410 nm, more preferably, from about 330 nm to about 390 nm, particularly preferably, from 350 nm or 370 nm. UV-absorbing materials such as a UV-absorbing solvent may be present during the method of photo-converting step provided that they do not absorb the particular preferable wavelength of UV light used for irradiation to the extent described above.

Further, the intensity of the UV light source is at least about 0.01-Watts per square centimeter ("W/cm²"), preferably at least about 0.1-W/cm², or is of sufficient intensity to produce a photo-epimerized mixture of enantiomers. The rate of photo-epimerization is proportional to the intensity of UV light from each high-intensity UV light source used or the number of UV light sources used, and inversely proportional to the distance between the UV light source and the component mentioned above. Preferably, the UV light source is LED light. Preferably, total power of the UV light source is up to about 120 W. More preferably, total power of the UV light is about 10 W to about 200 W.

Furthermore, the UV light source includes a UV spot lamp, a UV photoreactor, or a UV photoreactor flow through cell. A total of 1, 2, 4, 6, 8, 12, 20, 50, 100, 200 or more high intensity UV light sources may be used. When a UV photoreactor flow through cell is used in the invention method, the percent decrease of e.e. is inversely proportional to the flow rate of the mixture passed through the cell. A total of 1, 2, 4, 6, 8, 12, or more flow through photoreactor cells may be used.

UV light sources are readily available from commercial sources and for purposes of practicing the photo-epimerization method of the present invention. It does not matter which particular type or brand of UV light source is used.

The rate of photo-epimerization according to a method of this invention is believed to be inversely proportional to the concentration of the (2S)- or (2R)-enantiomer in a solution reaction mixture.

The concentration of the (2S)- or (2R)-enantiomer in the reaction mixture is typically more than 1 grams of the enantiomer per liter of solution ("g/L"), preferably, more than 10 g/L, more preferably, more than 20 g/L, particular preferably, more than 30 g/L although it may be lower.

The Compound of the Present Invention: Carboxylic Acid

The compound used in the present invention is directed to the substituted 2-trifluoromethyl-2H-chromene-3-carboxylic acid. Preferably, the compound is represented by the following formula I:

[Chem.5]

I wherein $R^1$ is one or more independently selected from halogen, $C_1$-$C_6$-alkyl or deutero-$C_1$-$C_6$-alkyl, $C_2$-$C_6$-alkenyl or deutero-$C_2$-$C_6$-alkenyl, $C_2$-$C_6$-alkynyl or deutero-$C_2$-$C_6$-alkynyl, $C_1$-$C_6$-alkoxy or deutero-$C_1$-$C_6$-alkoxy, $C_3$-$C_6$-cycloalkyl, $C_1$-$C_6$-alkoxy-$C_1$-$C_6$-alkyl, $C_1$-$C_6$-haloalkyl, $C_1$-$C_6$-haloalkoxy, amine, nitro, and cyano. The number of $R^1$ is preferably 1, 2, 3 or 4, more preferably, the number of $R^1$ is 1 or 2, particular preferably, the number of $R^1$ is 1.

The term "alkyl" as a group or part of a group e.g. alkoxy or hydroxyalkyl refers to a straight or branched alkyl group in all isomeric forms.

The term "$C_1$-$C_6$ alkyl" refers to an alkyl group, as a substituted $R^1$ of the compound in the formula I, containing at least 1, and at most 6 carbon atoms. Examples of such alkyl groups include methyl, ethyl, propyl, isopropyl, n-butyl, isobutyl, sec-butyl, tert-butyl, and the like.

The term "$C_2$-$C_6$ alkenyl" refers to an alkenyl group, as a substituted $R^1$ of the compound in the formula I, containing at least 2, and at most 6 carbon atoms. Examples of such alkenyl groups include vinyl, 1-propenyl, allyl, 1-butenyl, 2-butenyl, 3-butenyl, pentenyl, hexenyl, and the like.

The term "$C_2$-$C_6$ alkynyl", refers to an alkynyl group, as a substituted $R^1$ of the compound in the formula I, containing at least 2, and at most 6 carbon atoms. Examples of such alkynyl groups include ethynyl, 1-propynyl, 2-propynyl, 1-butynyl, 3-butynyl, pentynyl, hexynyl, and the like.

The term "$C_1$-$C_6$ alkoxy" refers to an alkoxy group containing at least 1, and at most 6 carbon atoms. Examples of such alkoxy groups include methoxy group, ethoxy group, normal propoxy group, isopropoxy group, normal butoxy group, secondary butoxy group, tertiary butoxy group, normal pentyl group, isopentyl group, tertiary pentyl group, neopentyl group, 2,3-dimethylpropyl group, 1-ethyl-propyl group, 1-methylbutyloxy group, normal hexyloxy group, isohexyloxy group, 1,1,2-trimethylpropyloxy group, and the like.

The term "halogen" refers to fluorine (F), chlorine (Cl), bromine (Br), or iodine (I), and the term "halo" refers to the halogen: fluoro (—F), chloro (—Cl), bromo (—Br), and iodo (—I).

For example, preferred compound of the present invention is as follows:

6-chloro-7-tert-butyl-2-trifluoromethyl-2H-chromene-3-carboxylic acid, 6-chloro-8-methyl-2-trifluoromethyl-2H-chromene-3-carboxylic acid, 6-chloro-8-ethyl-2-trifluoromethyl-2H-chromene-3-carboxylic acid, 6-chloro-5,7-dimethyl-2-trifluoromethyl-2H-chromene-3-carboxylic acid, 6,8-dimethyl-2-trifluoromethyl-2H-chromene-3-carboxylic acid, 6,8-dichloro-2-trifluoromethyl-2H-chromene-3-carboxylic acid, 8-ethyl-6-trifluoromethoxy-2-trifluoromethyl-2H-chromene-3-carboxylic acid, 6-bromo-8-methyl-2-trifluoromethyl-2H-chromene-3-carboxylic acid, or 6-bromo-8-(methyl-D3)-2-trifluoromethyl-2H-chromene-3-carboxylic acid.

For example, more preferred compound of the present invention is:

(S)-6-chloro-7-tert-butyl-2-trifluoromethyl-2H-chromene-3-carboxylic acid, (R)-6-chloro-7-tert-butyl-2-trifluoromethyl-2H-chromene-3-carboxylic acid, (S)-6,8-dichloro-2-trifluoromethyl-2H-chromene-3-carboxylic acid, (R)-6,8-dichloro-2-trifluoromethyl-2H-chromene-3-carboxylic acid, (S)-6-bromo-8-(methyl-D3)-2-trifluoromethyl-2H-chromene-3-carboxylic acid, or (R)-6-bromo-8-(methyl-D3)-2-trifluoromethyl-2H-chromene-3-carboxylic acid.

For example, the compound represented by formula (I) is described in U.S. Pat. No. 6,034,256 (also described in EP0977748, JP4577534, CN1196692, or KR10-0538258) and the like. A compound of formula (I) or a salt thereof can be easily prepared by known methods or known methods per se.

Isotopically-Labeled Compound

The present invention includes all pharmaceutically acceptable isotopically-labeled compounds of the present invention wherein one or more atoms are replaced by atoms having the same atomic number, but an atomic mass or mass number different from the atomic mass or mass number usually found in nature. Examples of isotopes suitable for inclusion in the compounds of the present invention include isotopes of hydrogen such as $^2$H and $^3$H, carbon such as $^{11}$C, $^{13}$C, and $^{14}$C, chlorine such as $^{38}$Cl, fluorine such as $^{18}$F, iodine such as $^{123}$I and $^{125}$I, nitrogen such as $^{13}$N and $^{15}$N, oxygen such as $^{15}$O, $^{17}$O and $^{18}$O, phosphorus such as $^{32}$P, and sulfur such as $^{35}$S.

Certain isotopically-labeled compounds of the present invention, for example, those incorporating a radioactive isotope, are useful in drug and/or substrate tissue distribution studies associated with cancer therapy which includes diagnosis, alleviation of symptoms, improvement of QOL, and prophylaxis. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O, and $^{13}$N, can be useful in Positron Emission Topography (PET) studies for examining substrate receptor occupancy.

Chiral Amine (i.e. Resolving Agent) Used in the Present Invention

Another aspect of this invention is the above method for separating enantiomers of a substituted 2-trifluoromethyl-2H-chromene-3-carboxylic acid by enantioselective fractional crystallization, wherein the method comprises contacting the substituted 2-trifluoromethyl-2H-chromene-3-carboxylic acid with a chiral amine to form a salt. For example, such chiral amines are as described in the following Tables 1 to 3.

TABLE 1

| | |
|---|---|
| (S)-(−)-alpha-methylbenzylamine | (R)-(+)-alpha-methylbenzylamine |
| (S)-(−)-2-amino-3-phenyl-1-propanol | (R)-(+)-2-amino-3-phenyl-1-propanol |
| (1R,2S)-(−)-2-amino-1,2-diphenylethanol | (1S,2R)-(+)-2-amino-1,2-diphenylethanol |
| (R)-(+)-4-(diphenylmethyl)-2-oxazolidinone | (S)-(−)-4-(diphenylmethyl)-2-oxazolidinone |
| (1R,2S)-(+)-cis-[2-(benzylamino)cyclohexyl]methanol | (1S,2R)-(−)-cis-[2-(benzylamino)cyclohexyl]methanol |
| L-phenylalaninol | D-phenylalaninol |
| (R)-(−)-2-amino-1-butanol | (S)-(+)-2-amino-1-butanol |
| (R)-(−)-2-phenylglycinol | (S)-(+)-2-phenylglycinol |
| (1R,2R)-(+)-1,2-diphenylethylenediamine | (1S,2S)-(−)-1,2-diphenylethylenediamine |
| (1S,2R)-(+)-norephedrine | (1R,2S)-(−)-norephedrine |
| (1R,2S)-(−)-N-methylephedrine | (1S,2R)-(+)-N-methylephedrine |
| (1R,2S)-(−)-ephedrine | (1S,2R)-(+)-ephedrine |
| (1R,2S)-(+)-1-amino-2-indanol | (1S,2R)-(−)-1-amino-2-indanol |
| (1R,2R)-(−)-2-amino-1-phenyl-1,3-propanediol | (1S,2S)-(+)-2-amino-1-phenyl-1,3-propanediol |
| (1R,2R)-(−)-2-amino-1-(4-nitrophenyl)-1,3-propanediol | (1S,2S)-(+)-2-amino-1-(4-nitrophenyl)-1,3-propanediol |
| (S)-(−)-N-benzyl-alpha-methylbenzylamine | (R)-(+)-N-benzyl-alpha-methylbenzylamine |
| L-amphetamine | D-amphetamine |

TABLE 1-continued

| | |
|---|---|
| (+)-deoxyephedrine | (−)-deoxyephedrine |
| (R)-(+)-1-(1-naphthyl)ethylamine | (S)-(−)-1-(1-naphthyl)ethylamine |
| (R)-(+)-1-phenylethylamine | (S)-(−)-1-phenylethylamine |
| (S)-(+)-1-cyclohexylethylamine | (R)-(−)-1-cyclohexylethylamine |
| (R)-(−)-2-pyrrolidinemethanol | (S)-(+)-2-pyrrolidinemethanol |
| (S)-(−)-alpha,alpha-diphenyl-2-pyrrolidinemethanol | (R)-(+)-alpha,alpha-diphenyl-2-pyrrolidinemethanol |
| (1S,2S)-(+)-pseudoephedrine | (1R,2R)-(−)-pseudoephedrine |
| (2R,3S)-(−)-4-dimethylamino-1,2-diphenyl-3-methyl-2-butanol | (2S,3R)-(+)-4-dimethylamino-1,2-diphenyl-3-methyl-2-butanol |
| (1R,2R,3R,5S)-(−)-isopinocampheylamine | (1S,2S,3S,5R)-(+)-isopinocampheylamine |
| (S)-(−)-2,2'-diamino-1,1'-binaphthyl | (R)-(+)-2,2'-diamino-1,1'-binaphthyl |
| (−)-sparteine | (+)-sparteine |
| L-phenylalaninamide | D-phenylalaninamide |
| (+)-cinchonine | (−)-cinchonine |
| (−)-cinchonidine | (+)-cinchonidine |
| (−)-brucine | (+)-brucine |
| (−)-quinine | (+)-quinine |
| (+)-quinidine | (−)-quinidine |
| (−)-strychnine | (+)-strychnine |
| (+)-dehydroabietylamine | (−)-dehydroabietylamine |
| (−)-cis-myrtanylamine | (+)-cis-myrtanylamine |
| (R)-(−)-2-amino-3-benzylthio-1-propanol | (S)-(+)-2-amino-3-benzylthio-1-propanol |
| (R)-(+)-bornylamine | (S)-(−)-bornylamine |
| L-(−)-alpha-amino-epsilon-caprolactam | D-(+)-alpha-amino-epsilon-caprolactam |

Further, more preferred chiral amines are as described in the following Table 2, for example,

TABLE 2

| | |
|---|---|
| (S)-(−)-2-amino-3-phenyl-1-propanol | (R)-(+)-2-amino-3-phenyl-1-propanol |
| L-phenylalaninol | D-phenylalaninol |
| (1R,2R)-(−)-2-amino-1-phenyl-1,3-propanediol | (1S,2S)-(+)-2-amino-1-phenyl-1,3-propanediol |
| (S)-(−)-N-benzyl-alpha-methylbenzylamine | (R)-(+)-N-benzyl-alpha-methylbenzylamine |
| (R)-(+)-1-(1-naphthyl)ethylamine | (S)-(−)-1-(1-naphthyl)ethylamine |
| (R)-(−)-2-pyrrolidinemethanol | (S)-(+)-2-pyrrolidinemethanol |
| L-phenylalaninamide | D-phenylalaninamide |
| (+)-cinchonine | (−)-cinchonine |
| (−)-cinchonidine | (+)-cinchonidine |

Further, particularly preferred chiral amines are described in the following Table 3, for example,

TABLE 3

| | |
|---|---|
| (S)-(−)-2-amino-3-phenyl-1-propanol | (R)-(+)-2-amino-3-phenyl-1-propanol |
| L-phenylalaninol | D-phenylalaninol |
| (1R,2R)-(−)-2-amino-1-phenyl-1,3-propanediol | (1S,2S)-(+)-2-amino-1-phenyl-1,3-propanediol |
| (S)-(−)-N-benzyl-alpha-methylbenzylamine | (R)-(+)-N-benzyl-alpha-methylbenzylamine |
| (R)-(+)-1-(1-naphthyl)ethylamine | (S)-(−)-1-(1-naphthyl)ethylamine |
| (R)-(−)-2-pyrrolidinemethanol | (S)-(+)-2-pyrrolidinemethanol |
| L-phenylalaninamide | D-phenylalaninamide |
| (+)-cinchonine | (−)-cinchonine |
| (−)-cinchonidine | (+)-cinchonidine |

The current invention allows to obtain an optically pure (S)- or (R)-form of the carboxylic acid from the racemate by selecting the chirality of the corresponding amine.

Solvents Used in the Present Invention

The solvents used here may be selected from the group consisting of $C_5$-$C_{10}$ aliphatic hydrocarbons (for example, hexane, heptane, octane, cyclohexane, cycloheptane, etc.), aromatic hydrocarbons (for example, benzene, toluene, xylene, etc.), $C_1$-$C_6$ alcohols (for example, methanol, ethanol, 2-propanol, butanol, hexanol, etc.), $C_2$-$C_8$ ethers (for example, diethyl ether, diisopropyl ether, tert-butyl methyl ether, tetrahydrofuran, 2-methyltetrahydrofuran, dioxane, etc.), $C_3$-$C_8$ ketones (for example, acetone, methyl ethyl ketone, etc.), $C_2$-$C_8$ esters (for example, ethyl acetate, isopropyl acetate, etc.), $C_1$-$C_6$ halogenated hydrocarbons (for example, dichloromethane, chloroform, etc.), nitriles (for example, acetonitrile, etc.), acid amides (for example, N,N-dimethylformamide, etc.), lactams (for example, N-methylpyrrolidone, etc.), sulfoxides (for example, dimethyl sulfoxide, etc.), water, and a mixture of two or more thereof.

Examples of particularly preferred solvents are hexane, heptane, toluene, ethanol, 2-propanol, diisopropyl ether, tert-butyl methyl ether, tetrahydrofuran, 2-methyltetrahydrofuran, acetone, methyl ethyl ketone, ethyl acetate, dichloromethane, acetonitrile, N,N-dimethylformamide, water, and mixtures of two or more of these.

A suitable chiral amine and/or solvent for salt formation can be identified by the use of a screening approach. In a primary screen, variable and unique combinations of chiral amines and solvent are combined in separate containers with a given substituted 2-trifluoromethyl-2H-chromene-3-carboxylic acid. The presence of a salt as a precipitate can be determined by visual inspection after an incubation period, at a given time and temperature that proceeds the epimerization reaction. The precipitated salts can then be evaluated by chiral HPLC to determine the enantiomeric excess. From the most promising candidate combinations from the primary screen, a secondary screen can subsequently be performed at a larger scale to determine the recovery yield of the precipitate, the extent of conversion, and purity. It is easy for those skilled in the art.

Preferred Combination of Compound, Chiral Amines, and Solvents

Examples of particularly preferred combination of a compound and solvent are:

6-chloro-7-tert-butyl-2-trifluoromethyl-2H-chromene-3-carboxylic acid and acetonitrile, 6-chloro-7-tert-butyl-2-trifluoromethyl-2H-chromene-3-carboxylic acid and tert-butyl methyl ether, 6-chloro-7-tert-butyl-2-trifluoromethyl-2H-chromene-3-carboxylic acid and 2-propanol, 6-chloro-7-tert-butyl-2-trifluoromethyl-2H-chromene-3-carboxylic acid and heptane, or 6-chloro-7-tert-butyl-2-trifluoromethyl-2H-chromene-3-carboxylic acid and about 1:1 (v/v) mixture of ethanol and water.

Examples of particularly preferred combination of a compound and chiral amine are:

6-chloro-7-tert-butyl-2-trifluoromethyl-2H-chromene-3-carboxylic acid and (S)-(−)- or (R)-(+)-2-amino-3-phenyl-1-propanol, 6-chloro-7-tert-butyl-2-trifluoromethyl-2H-chromene-3-carboxylic acid and L- or D-phenylalaninol, 6-chloro-7-tert-butyl-2-trifluoromethyl-2H-chromene-3-carboxylic acid and (1R,2R)-(−)- or (1S,2S)-(+)-2-amino-1-phenyl-1,3-propanediol, 6-chloro-7-tert-butyl-2-trifluoromethyl-2H-chromene-3-carboxylic acid and (S)-(−)- or (R)-(+)-N-benzyl-alpha-methylbenzylamine, 6-chloro-7-tert-butyl-2-trifluoromethyl-2H-chromene-3-carboxylic acid and (R)-(+)- or (S)-(−)-1-(1-naphthyl)ethylamine, 6-chloro-7-tert-butyl-2-trifluoromethyl-2H-chromene-3-carboxylic acid and (R)-(−)- or (S)-(+)-2-pyrrolidinemethanol, 6-chloro-7-tert-butyl-2-trifluoromethyl-2H-chromene-3-carboxylic acid and L- or D-phenylalaninamide, 6-chloro-7-tert-butyl-2-trifluoromethyl-2H-chromene-3-carboxylic acid and (+)- or (−)-cinchonine, or 6-chloro-7-tert-butyl-2-trifluoromethyl-2H-chromene-3-carboxylic acid and (−)- or (+)-cinchonidine.

Examples of particularly preferred combination of a compound, chiral amines, and solvents are:

6-chloro-7-tert-butyl-2-trifluoromethyl-2H-chromene-3-carboxylic acid, (S)-(−)- or (R)-(+)-2-amino-3-phenyl-1-propanol, and acetonitrile, 6-chloro-7-tert-butyl-2-trifluoromethyl-2H-chromene-3-carboxylic acid, (S)-(−)- or (R)-(+)-2-amino-3-phenyl-1-propanol, and tert-butyl methyl ether, 6-chloro-7-tert-butyl-2-trifluoromethyl-2H-chromene-3-carboxylic acid, (S)-(−)- or (R)-(+)-2-amino-3-phenyl-1-propanol, and heptane, 6-chloro-7-tert-butyl-2-trifluoromethyl-2H-chromene-3-carboxylic acid, L- or D-phenylalaninol, and acetonitrile, 6-chloro-7-tert-butyl-2-trifluoromethyl-2H-chromene-3-carboxylic acid, L- or D-phenylalaninol, and tert-butyl methyl ether, 6-chloro-7-tert-butyl-2-trifluoromethyl-2H-chromene-3-carboxylic acid, L- or D-phenylalaninol, and heptane, 6-chloro-7-tert-butyl-2-trifluoromethyl-2H-chromene-3-carboxylic acid, L- or D-phenylalaninamide, and 2-propanol, 6-chloro-7-tert-butyl-2-trifluoromethyl-2H-chromene-3-carboxylic acid, (S)-(−)- or (R)-(+)-N-benzyl-alpha-methylbenzylamine, and 1:1 (v/v) mixture of ethanol and water, 6-chloro-7-tert-butyl-2-trifluoromethyl-2H-chromene-3-carboxylic acid, (1R,2R)-(−)- or (1S,2S)-(+)-2-amino-1-phenyl-1,3-propanediol, and acetonitrile, or 6-chloro-7-tert-butyl-2-trifluoromethyl-2H-chromene-3-carboxylic acid, (R)-(+)- or (S)-(−)-1-(1-naphthyl)ethylamine, and acetonitrile.

Conversion progress can be monitored to determine if the process is sufficiently complete. The process is judged to be complete when the enantiomeric ratio is detected to meet the criteria set by the experimenter. These criteria are met in a preferred embodiment when the mixture is converted to a thermodynamic equilibrium mixture. A preferred method of HPLC analysis uses a chiral column to separate the enantiomers.

The formula to calculate enantiomeric excess (% e.e.) is typically as follows:

$$\text{Enantiomeric excess (\% e.e.)} = \frac{[\text{major enantiomer}] - [\text{minor enantiomer}]}{[\text{major enantiomer}] + [\text{minor enantiomer}]} \times 100 \quad [\text{Math. 1}]$$

Use of the Present Invention

Generally, the compound of the present invention is known to be useful as cyclooxygenase-2 (COX-2) inhibitor (U.S. Pat. No. 6,034,256). Thus, the present compound is effective for treatment of diseases mediated by cyclooxygenase-2, such as inflammation, pain, cancer, fever, osteoarthritis, rheumatoid arthritis, migraine, neurodegenerative diseases, cardiovascular disease, osteoporosis, asthma, lupus and psoriasis, dysmenorrhea, premature labor, gout, ankylosing spondylitis, bursitis, heat burn, sprain, and contusion (Inflamm Res 2000, 49, 367-92).

Particularly, a compound of (S)-6-chloro-7-tert-butyl-2-trifluoromethyl-2H-chromene-3-carboxylic acid of the present invention is useful in the following points: (1) a powerful non-narcotic analgesic property, (2) excellent immediate effect and sustainability, and (3) newly adaptation to neuropathic pain are expected, and (4) safety problems of gastrointestinal devices, kidneys, and cardiovascular systems which are problematic with existing drugs are not observed.

Administration

The present compound can be administered orally or parenterally. Examples of the mode of administration include oral administration, ophthalmic topical administration, intravenous administration and transdermal administration, and the present compound can be formulated into a preparation suitable for such an administration mode by properly selecting and using a pharmaceutically acceptable additive as needed.

Examples of the dosage form include, in the case of an oral preparation, a tablet, a capsule, a granule, and a powder, and, in the case of a parenteral preparation, an injection, an eye drop, an eye ointment, an insert, and an intraocular implant.

The dose of the present compound can be properly selected depending on the dosage form, symptoms, age, body weight of a patient, or the like. For example, in the case of oral administration, it can be administered in an amount of from about 0.01 mg to about 5000 mg, preferably from about 0.1 mg to about 2500 mg, particularly preferably from about 0.5 mg to about 1000 mg per day in a single dose or several divided doses. In the case of an injection, it can be administered in an amount of from about 0.00001 mg to about 2000 mg, preferably from about 0.0001 to about 1500 mg, particularly preferably from about 0.001 mg to about 500 mg per day in a single dose or several divided doses.

Pharmaceutical Composition

The compounds of the invention are conveniently administered in the form of a pharmaceutical composition for treatment of inflammation or pain etc. Such composition may conveniently be presented for use in conventional manner in admixture with one or more pharmaceutically acceptable carriers or excipients.

While it is possible for the compounds of the invention to be administered as the raw chemical, it is preferable to present it as a pharmaceutical composition in the form of a pharmaceutical formulation. The formulations comprise the compounds together with one or more acceptable carriers or diluents, and optionally other therapeutic ingredients. The carrier(s) must be "acceptable" in the sense of being compatible with the other ingredients of the formulation and not deleterious to the recipient thereof.

A pharmaceutical composition is formulated to meet the desirable route of administration. The administration route is, for example, parenteral (e.g., intravenous, in the skin, subcutaneous), oral (e.g., ingestion or inhalation), percutaneous (local), mucosal, rectum, and local (including percutaneous, oral, and sublingual) administration. A pharmaceutical composition formulated in the form of a solution or suspension can be prepared by the method described in, for example, Remington's Pharmaceutical Sciences, 18th ed., Gennaro, ed., Mack Publishing Co., Easton, Pa., (1990) or according to common technical knowledge in the art.

EXAMPLE

Representative examples of the method of the present invention are described below. Enantiomeric excess (e.g., chiral purities) for Examples 1 to 15 was determined by enantioselective high-pressure liquid chromatography (HPLC) method described below in Chiral HPLC analysis. Absolute stereochemistries reported below were determined by comparison of enantioselective HPLC retention times to those for the exact reference standards.

Analytical Equipment and Conditions
NMR:
Instrument: Agilent MercuryPlus 300
Magnet: 7.05 Tesla magnet from Oxford instruments, S/N: 175057 B0597 DLN2273405
Probe: 4 nuclei auto switchable $^{1}H/^{19}F/^{13}C/^{31}P$, $^{1}H/^{19}F/\{^{15}N-^{31}P\}$, Part. no. 01-904083-05, S/N: P007331
Console: Mercury plus console, S/N: 5012240
Temperature: Temperature controller without low temperature unit
Hard/software: HP z420 computer with VNMRJ 4.2a software
Chiral HPLC method: 30123 PDR
Instrument: Agilent 1100 series with UV detector and polarimeter
Column: Chiralpak IA (4.6×250 mm, 5 microm)
Pump Flow: 0.7 mL/min
UV Detection: 242 nm and 286 nm
Injection Volume: 1 microL
Run Time: 12 min.
Mobile Phase: Heptane/ethanol/trifluoroacetic acid (90/10/0.2)

Sample preparation: About 1 mg salt was taken up in HPLC-grade EtOH (about 1 mL), liberated over an Si-SCX-2 ion exchanger (Silicycle, product number: SPE-R51230B-01C) and analyzed as such.

Retention time: (R)-6-chloro-7-tert-butyl-2-trifluoromethyl-2H-chromene-3-carboxylic acid: 6.177 min,
(S)-6-chloro-7-tert-butyl-2-trifluoromethyl-2H-chromene-3-carboxylic acid: 7.008 min
HPLC method: 30123 TFA LCMS-5 C8
Instrument: Agilent 1290 series with UV detector and HP 6130 MSD mass detector
Column: Zorbax RRHD SB C8 (2.1×50 mm, 1.8 microm)
Mobile phase A: Trifluoroacetic acid (aq; 0.05%)
Mobile phase B: Acetonitrile
Pump Flow: 0.6 mL/min
UV Detection: 215 nm and 254 nm
Injection Volume: 0.2 microL
Run Time: 3.0 min

| Pump Program: | Gradient: | | |
| --- | --- | --- | --- |
| | Time (min) | % A | % B |
| | 0.0 | 80 | 20 |
| | 1.5 | 10 | 90 |

Column Temp.: 35° C.
Mass Detection: API-ES positive and negative
Sample preparation: About 1 mg material was taken up in HPLC-grade methanol (about 1 mL) and analyzed as such against a blank sample.

Retention time: (S)-2-amino-3-phenyl-1-propanol: 0.350 min. (R)- or
(S)-6-chloro-7-tert-butyl-2-trifluoromethyl-2H-chromene-3-carboxylic acid: 1.563 min.

The Experimental Procedure of Example 1 to 12

The compounds disclosed hereinafter were prepared according to the following procedure:

To a magnetically stirred suspension of (+/−)-6-chloro-7-tert-butyl-2-trifluoromethyl-2H-chromene-3-carboxylic acid (1.0 eq) in a single solvent or mixture of solvents was added a chiral amine (1.0 eq) as resolving agent in a reactor in a fume hood with the light switched off. The mixture was heated resulting in a clear solution. After cooling, the suspension was sampled and the solid and filtrate were analyzed by chiral HPLC.

The reactor was placed in a box containing eight LEDs (370 nm at a total power of ~120 W) and the suspension was irradiated in this box at 20° C. (Example 1-6 and 8-12) or 0° C. (Example 7). The irradiation was continued until the filtrate was essentially racemic. The solid was collected by filtration and the filter cake was recrystallized from or washed with a single solvent or mixture of solvents as necessary. The solid was dried in vacuo to furnish the salt.

Example 1

Scale: 0.5 mmol
Resolving agent: (S)—N-Benzyl-alpha-methylbenzylamine
Solvent: Ethanol and Water (1:1 (v/v), 7.5 mL)
Temperature 20° C.

TABLE 4

| Entry | Irradiation time | Solid enantiomeric excess (% e.e.) | Filtrate enantiomeric excess (% e.e.) | Yield (%) |
|---|---|---|---|---|
| 1a | Start | (S) 22.4 | (R) 70.7 | 76[a] |
| 1b | 3 h 20 m | (S) 93.0 | (R) 6.5 | 65[b] |
| 1c | none | (S) 99.3 | n.d.[c] | 57[b] |

Entry 1b solid was recrystallized from a mixture (1:1 (v/v)) of ethanol and water (8.0 mL) to afford 1c.
[a]Calculated.
[b]Isolated by filtration and drying (no washing). Not corrected for sampling.
[c]Not determined.

Example 2

Scale: 1.0 mmol
Resolving agent: (1R,2R)-2-Amino-1-phenyl-1,3-propanediol
Solvent: Acetonitrile (5 mL)
Temperature 20° C.

TABLE 5

| Entry | Irradiation time | Solid enantiomeric excess (% e.e.) | Filtrate enantiomeric excess (% e.e.) | Yield (%) |
|---|---|---|---|---|
| 2a | Start | (S) 83.8 | (R) 72.7 | 46[a] |
| 2b | 1 h 10 m | (S) 89.5 | (R) 55.1 | — |
| 2c | 2 h 40 m | (S) 93.7 | (R) 17.5 | — |
| 2d | 4 h 00 m | (S) 96.0 | (R) 1.4 | 61[b] |
| 2e | none | (S) 99.5 | n.d.[c] | 52[b] |

Entry 2d solid was recrystallized from acetonitrile (16 mL) to afford 2e.
[a]Calculated.
[b]Isolated by filtration and drying (no washing). Not corrected for sampling.
[c]Not determined.

Example 3

Scale: 0.67 mmol
Resolving agent: (R)-1-(1-Naphthyl)ethylamine
Solvent: Acetonitrile (10 mL)
Temperature 20° C.

TABLE 6

| Entry | Irradiation time | Solid enantiomeric excess (% e.e.) | Filtrate enantiomeric excess (% e.e.) | Yield (%) |
|---|---|---|---|---|
| 3a | Start | (S) 6.9 | (R) 45.4 | 87[a] |
| 3b | 2 h 25 m | (S) 49.6 | (R) 26.7 | — |
| 3c | 4 h 20 m | (S) 83.3 | (R) 21.0 | — |
| 3d | 5 h 40 m | (S) 89.5 | (S) 2.0 | 65[b] |
| 3e | none | (S) 99.2 | n.d.[c] | 55[b] |

Entry 3d solid was recrystallized from acetonitrile (14 mL) to afford 3e.
[a]Calculated.
[b]Isolated by filtration and drying (no washing). Not corrected for sampling.
[c]Not determined.

Example 4

Scale: 0.5 mmol
Resolving agent: (S)-2-Amino-3-phenyl-1-propanol
Solvent: Acetonitrile (10 mL)
Temperature 20° C.

TABLE 7

| Entry | Irradiation time | Solid enantiomeric excess (% e.e.) | Filtrate enantiomeric excess (% e.e.) | Yield (%) |
|---|---|---|---|---|
| 4a | Start | (S) 19.1 | (R) 46.9 | 71[a] |
| 4b | 2 h 40 m | (S) 95.8 | (S) 1.0 | 75[b] |
| 4c | none | (S) 98.7 | n.d.[c] | 65[b] |

Entry 4b solid was recrystallized from acetonitrile (7.0 mL) to afford 4c.
[a]Calculated.
[b]Isolated by filtration and drying (no washing). Not corrected for sampling.
[c]Not determined.

Example 5

Scale: 4.0 mmol
Resolving agent: (S)-2-Amino-3-phenyl-1-propanol
Solvent: tert-Butyl methyl ether (10 mL)
Temperature 20° C.

TABLE 8

| Entry | Irradiation time | Solid enantiomeric excess (% e.e.) | Filtrate enantiomeric excess (% e.e.) | Yield (%) |
|---|---|---|---|---|
| 5a | Start | (S) 22.1 | (R) 39.4 | 64[a] |
| 5b | 4 h 15 m | (S) 58.3 | (R) 24.3 | — |
| 5c | 8 h 25 m | (S) 71.0 | (R) 22.8 | — |
| 5d | 17 h 35 m | (S) 81.4 | (R) 13.4 | — |

[a]Calculated.

Example 6

Scale: 1.0 mmol
Resolving agent: L-Phenylalaninamide
Solvent: Isopropyl alcohol (5 mL)
Temperature 20° C.

TABLE 9

| Entry | Irradiation time | Solid enantiomeric excess (% e.e.) | Filtrate enantiomeric excess (% e.e.) | Yield (%) |
|---|---|---|---|---|
| 6a | Start | (S) 85.8 | (R) 54.4 | 39[a] |
| 6b | 3 h 45 m | (S) 88.7 | (S) 5.2 | 63[b] |
| 6c | none | (S) 98.5 | n.d.[c] | 54[b] |

Entry 6b solid was recrystallized from isopropyl alcohol (3.0 mL) to afford 6c.
[a]Calculated.
[b]Isolated by filtration and drying (no washing). Not corrected for sampling.
[c]Not determined.

Example 7

Scale: 0.5 mmol
Resolving agent: (S)-2-Amino-3-phenyl-1-propanol
Solvent: Acetonitrile (10 mL)
Temperature 0° C.

TABLE 10

| Entry | Irradiation time | Solid enantiomeric excess (% e.e.) | Filtrate enantiomeric excess (% e.e.) | Yield (%) |
|---|---|---|---|---|
| 7a | Start | (S) 5.7 | (R) 29.0 | 84[a] |
| 7b | 2 h 40 m | (S) 18.2 | (R) 4.1 | — |
| 7c | 4 h 15 m | (S) 27.0 | (R) 21.0 | — |
| 7d | 12 h 25 m | (S) 96.5 | (S) 1.2 | 65[b] |

[a]Calculated.
[b]Isolated by filtration and drying (no washing). Not corrected for sampling.

Example 8

Scale: 14.9 mmol
Resolving agent: (S)-2-Amino-3-phenyl-1-propanol
Solvent: Acetonitrile (300 mL)
Temperature 20° C.

TABLE 11

| Entry | Irradiation time | Solid enantiomeric excess (% e.e.) | Filtrate enantiomeric excess (% e.e.) | Yield (%) |
|---|---|---|---|---|
| 8a | 2 h 00 m | (S) 27.1 | (R) 29.7 | — |
| 8b | 4 h 00 m | (S) 52.1 | (R) 31.4 | — |
| 8c | 8 h 00 m | (S) 97.0 | (R) 25.5 | — |
| 8d | 8 h 30 m | (S) 97.4 | (R) 22.5 | — |
| 8e | 12 h 30 m | (S) 98.2 | (R) 2.8 | — |
| 8f | none | (S) 99.0[d] | — | 80[d] |

Entry 8e solid was washed with acetonitrile (10 mL) and dried to afford 8f.
[d]After isolation by filtration, thing with 2 V (10 mL) acetonitrile and drying.

Example 9

Scale: 2.0 mmol
Resolving agent: (S)-2-Amino-3-phenyl-1-propanol
Solvent: Acetonitrile (1.3 mL) and tert-Butyl methyl ether (5.4 mL)
Temperature 20° C.

TABLE 12

| Entry | Irradiation time | Solid enantiomeric excess (% e.e.) | Filtrate enantiomeric excess (% e.e.) | Yield (%) |
|---|---|---|---|---|
| 9a | Start | (S) 12.3 | (R) 52.7 | 81[a] |
| 9b | 2 h 00 m | (S) 49.0 | (R) 51.5 | — |
| 9c | 4 h 00 m | (S) 89.4 | (R) 51.9 | — |
| 9d | 8 h 00 m | (S) 96.1 | (S) 0.6 | 62[b] |

[a]Calculated.
[b]Isolated by filtration and drying (no washing). Not corrected for sampling.

Example 10

Scale: 2.0 mmol
Resolving agent: (S)-2-Amino-3-phenyl-1-propanol
Solvent: Acetonitrile (6.7 mL)
Temperature 20° C.

TABLE 13

| Entry | Irradiation time | Solid enantiomeric excess (% e.e.) | Filtrate enantiomeric excess (% e.e.) | Yield (%) |
|---|---|---|---|---|
| 10a | Start | (S) 2.0 | (R) 47.1 | 96[a] |
| 10b | 4 h 25 m | (S) 25.4 | (R) 37.2 | — |
| 10c | 12 h 25 m | (S) 91.1 | (R) 51.6 | — |
| 10d | 16 h 25 m | (S) 98.0 | (S) 4.4 | 72[b] |

[a]Calculated.
[b]Isolated by filtration and drying (no washing). Not corrected for sampling.

Example 11

Scale: 2.0 mmol
Resolving agent: (S)-2-Amino-3-phenyl-1-propanol
Solvent: Acetonitrile (6.4 mL) and Water (0.3 mL)
Temperature 20° C.

TABLE 14

| Entry | Irradiation time | Solid enantiomeric excess (% e.e.) | Filtrate enantiomeric excess (% e.e.) | Yield (%) |
|---|---|---|---|---|
| 11a | Start | (S) 81.7 | (R) 43.2 | 35[a] |
| 11b | 3 h 55 m | (S) 92.8 | (R) 40.2 | — |
| 11c | 6 h 30 m | (S) 97.1 | (R) 3.9 | 59[b] |

[a]Calculated.
[b]Isolated by filtration and drying (no washing). Not corrected for sampling.

Example 12

Scale: 2.0 mmol
Resolving agent: (S)-2-Amino-3-phenyl-1-propanol
Solvent: Heptane (10 mL)
Temperature 20° C.

TABLE 15

| Entry | Irradiation time | Solid enantiomeric excess (% e.e.) | Filtrate enantiomeric excess (% e.e.) | Yield (%) |
|---|---|---|---|---|
| 12a | Start | (S) 1.0 | (R) 43.0 | 98[a] |
| 12b | 14 h 35 m | (S) 46.2 | (R) 21.4 | — |
| 12c | 24 h 32 m | (S) 84.0 | (R) 37.7 | — |
| 12d | 32 h 22 m | (S) 86.3 | (R) 8.2 | 70[g] |

[a]Calculated.
[g]After isolation by filtration, rinsing test tube with 7.5 V (5.0 mL) heptane and drying.

Example 13

Asymmetric transformation of 6-chloro-7-tert-butyl-2-trifluoromethyl-2H-chromene-3-carboxylic acid with (S)-2-amino-3-phenyl-1-propanol, slow addition of chiral amine A suspension of (+/−)-6-chloro-7-tert-butyl-2-trifluoromethyl-2H-chromene-3-carboxylic acid (5.00 g, 14.9 mmol) in acetonitrile (100 mL) was magnetically stirred in a reactor in a fume hood with the light switched off. The mixture was treated with (S)-2-amino-3-phenyl-1-propanol (904 mg, 0.4 eq, 5.98 mmol) and heated resulting a clear solution. After cooling, the suspension was sampled and the solid and filtrate analyzed by chiral HPLC (13a).

The reactor was placed in a box containing eight LEDs (370 nm at a total power of ~120 W) and the suspension was irradiated in this box at 20° C. After 30 min, the suspension was sampled and the solid and filtrate were analyzed by chiral HPLC (13b), and a solution of (S)-2-amino-3-phenyl-1-propanol (1.36 g, 0.6 eq, 8.96 mmol) in acetonitrile (200 mL) was added slowly into the mixture over 10 h period (addition rate: ca. 333 µL/min) with irradiation. The suspension was sampled twice (2 hours 30 minutes (13c) and 5 hours 40 minutes (13d) after the slow addition started) and the solid and filtrate were analyzed by chiral HPLC.

After 12 hours 30 minutes (13e), the irradiation was stopped and the solid was collected by filtration and washed with acetonitrile (10 mL). The solid was dried in vacuo to furnish the salt (5.88 g, 81% yield, 99.0% e.e.).

TABLE 16

| Entry | (S)-2-Amino-3-phenylpropan-1-ol | Acetonitrile (mL) | Irradiation time | Solid enantiomeric excess (% e.e.) | Filtrate enantiomeric excess (% e.e.) | Yield (%) |
|---|---|---|---|---|---|---|
| 13a | 0.4 eq | 100 | Start | (S) 85.0 | (R) 25.0 | 23[a] |
| 13b | No addition, only irradiation | 100 | 0 h 30 m | (S) 84.4 | (R) 14.6 | — |
| 13c | Additional 0.12 eq, Total: 0.52 eq | 140[e] | 2 h 30 m | (S) 94.0 | (R) 12.8 | — |
| 13d | Additional 0.19 eq, Total: 0.71 eq | 204[e] | 5 h 40 m | (S) 97.0 | (R) 8.8 | — |
| 13e | Additional 0.29 eq. Total: 1.0 eq | 300[e] | 12 h 30 m[f] | (S) 99.0 | (R) 0.9 | 81[d] |

[a]Calculated.
[d]After isolation by filtration, washing with 2 V (10 mL) acetonitrile and drying.
[e]Total volume of acetonitrile in the reactor.
[f]Upon complete addition the reaction was irradiated for another 2 hours.

Example 14

Asymmetric transformation of 6-chloro-7-tert-butyl-2-trifluoromethyl-2H-chromene-3-carboxylic acid with (S)-2-amino-3-phenyl-1-propanol A suspension of (+/−)-6-chloro-7-tert-butyl-2-trifluoromethyl-2H-chromene-3-carboxylic acid (5.00 g, 14.9 mmol) in acetonitrile (150 mL, Fischer Scientific, Code: A/0627/17, CAS: 75-05-8) was magnetically stirred in a thermostated (20° C.) 350 mL glass jacketed reactor in a fume hood with the light switched off. To the mixture was added (S)-2-amino-3-phenyl-1-propanol (2.26 g, 1.0 eq, 14.9 mmol, Combi-blocks, Code: OR-1076, CAS: 3182-95-4). The resulting mixture became a clear solution. After 5 minutes, a thick white suspension was observed which became thinner upon prolonged stirring. After being stirred overnight, the suspension was sampled. The sample was filtered and the solid and filtrate analyzed by chiral HPLC (method: 30123 PDR). The reactor was placed in a box containing eight LEDs (370 nm at a total power of ~120 W, unbranded) and the suspension was irradiated in this box. The progress of the asymmetric transformation was followed in time until the filtrate was essentially racemic:

TABLE 17

| Irradiation time | Solid enantiomeric excess (% e.e.) | Filtrate enantiomeric excess (% e.e.) |
|---|---|---|
| Start | (S) 4.9 | (R) 38.1 |
| 5 h 10 m | (S) 28.5 | (R) 30.0 |

TABLE 17-continued

| Irradiation time | Solid enantiomeric excess (% e.e.) | Filtrate enantiomeric excess (% e.e.) |
|---|---|---|
| 9 h 05 m | (S) 58.9 | (R) 23.4 |
| 12 h 30 m | (S) 92.3 | (R) 41.0 |
| 18 h 15 m | (S) 97.7 | (S) 2.9 |

After 18 h 15 m the irradiation was stopped and the suspension was allowed to stir at 20° C. overnight. The solid was collected by filtration and washed with acetonitrile (10 mL, Fischer Scientific, Code: A/0627/17). The solid was dried in vacuo on the rotary evaporator (10 mBar, 45° C.) for about 30 minutes to furnish the salt as a white solid (6.19 g, 85% yield).

Figure 5:
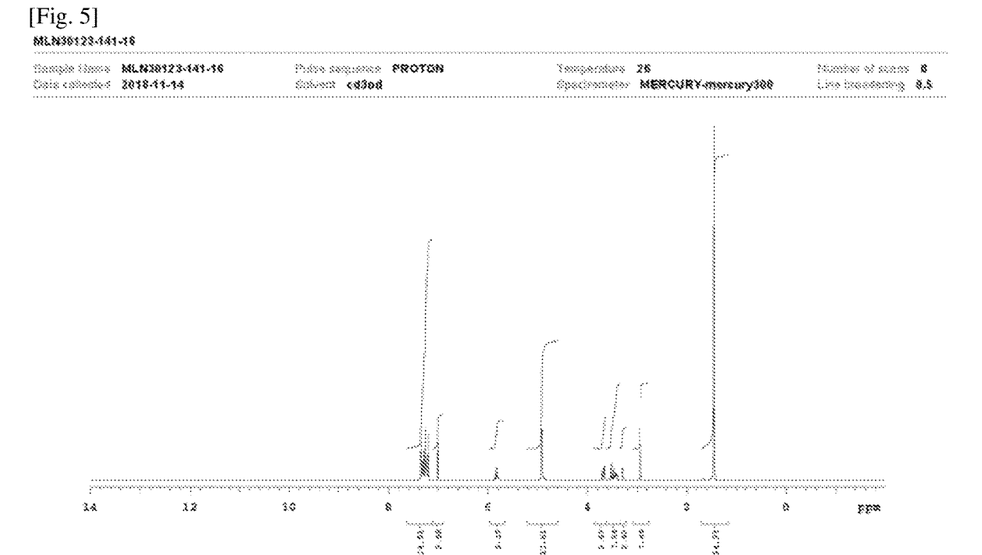
FIG. 5 shows $^1$H-NMR spectra of 6-chloro-7-tert-butyl-2-trifluoromethyl-2H-chromene-3-carboxylic acid and (S)-2-amino-3-phenyl-1-propanol salt in methanol-$d_4$ (i.e. $CD_3OD$).
Figure 6:
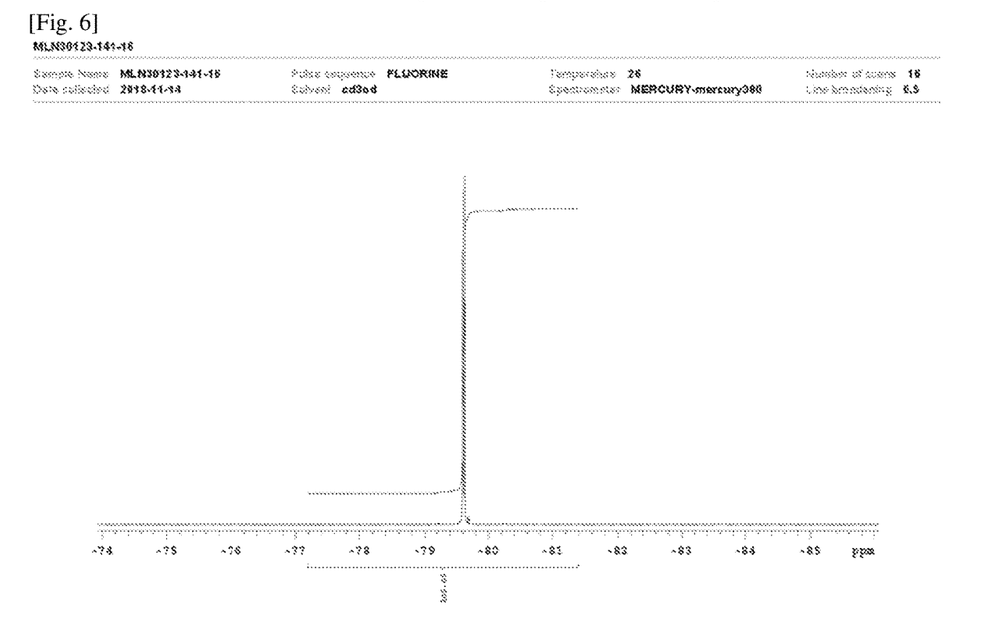
FIG. 6 shows $^{19}$F-NMR spectra of 6-chloro-7-tert-butyl-2-trifluoromethyl-2H-chromene-3-carboxylic acid and (S)-2-amino-3-phenyl-1-propanol salt in methanol-$d_4$ (i.e. $CD_3OD$).

The total amount of impurities in the solid as analyzed by HPLC-MS (method: 30123 TFA LCMS-5 C8) was: 0.00% (215 nm), 0.22% (238 nm). The total amount of impurities in the filtrate as analyzed by HPLC-MS (method: 30123 TFA LCMS-5 C8) was: 35.17% (215 nm), 9.87% (238 nm). The optical purity of the solid was 98.9% e.e. (S) (method: 30123 PDR). $^1$HNMR did not show residual solvent: $^1$H-NMR (methanol-$d_4$): FIG. 5; $^{19}$F-NMR (methanol-$d_4$): FIG. 6.

Example 15

Preparation of (S)-6-Chloro-7-tert-butyl-2-trifluoromethyl-2H-chromene-3-carboxylic acid by decomposition of salt A solid salt of (S)-6-chloro-7-tert-butyl-2-trifluoromethyl-2H-chromene-3-carboxylic acid and (S)-2-amino-3-phenyl-1-propanol (3.00 g, 6.17 mmol) was dissolved in ethyl acetate (100 mL) and washed with 1 N hydrochloric acid (50 mL) and brine (2×50 mL). The organic phase was dried over sodium sulfate and concentrated in vacuo yielding the title compound as a white solid (2.00 g, 97%): mp 175.0-176.0° C.; $^1$H-NMR (acetone-$d_6$) δ 7.86 (s, 1H), 7.52 (s, 1H), 7.12 (s, 1H), 5.83 (q, 1H, J=7.1 Hz), 1.48 (s, 9H), a peak of COOH was not observed. This compound was determined to have an optical purity of 99% e.e.

INDUSTRIAL APPLICABILITY

The present invention provides a method for preparing an optically active carboxylic acid from its racemate with high yield and high optical purity without optical resolution by utilizing the solubility difference in the diastereomeric salts of the racemic carboxylic acid and an optically active amine under UV light irradiation capable of affecting epimerization. Further, the present method is characterized by that a single optically active substance can be obtained from a racemate with a high yield of 80% or more. This makes sharp contrast with a known conventional optical resolution in which the upper limit of the yield is 50% or less. The additional advantage of this method lies in the fact that the chiral amine auxiliary does not react per se and can be recovered after isolation of the desired optically active carboxylic acid. Further, as long as both forms of chiral amine are available, either of the carboxylic acid isomers can be obtained depending on the chiral amine used ((+) or (−)) under otherwise identical reaction conditions.

The invention claimed is:

1. An asymmetric transformation method of enriching a desired isomer of a substituted 2-trifluoromethyl-2H-chromene-3-carboxylic acid, comprising:
   (a) in a solvent or mixture of solvents, contacting the substituted 2-trifluoromethyl-2H-chromene-3-carboxylic acid with a chiral amine to form salts, wherein the chiral amine is selected so that the solubility of the amine salt of the undesired substituted 2-trifluoromethyl-2H-chromene-3-carboxylic acid is greater than the amine salt of the desired substituted 2-trifluoromethyl-2H-chromene-3-carboxylic acid,
   (b) irradiating the transformation mixture with an ultraviolet (UV) light, wherein the irradiation increases the amount of the less soluble chiral amine salt of the substituted of the 2-trifluoromethyl-2H-chromene-3-carboxylic acid in the transformation mixture,
   (c) maintaining the irradiation for a period of time effective to increase the amount of the desired chiral amine salt of the substituted 2-trifluoromethyl-2H-chromene-3-carboxylic acid isomer,
   (d) separating the desired chiral amine salt of the substituted 2-trifluoromethyl-2H-chromene-3-carboxylic acid from the mixture, and
   (e) liberating the free form of the desired chiral substituted-2-trifluoromethyl-2H-chromen-3-carboxylic acid from the chiral amine salt by treatment with an acid,
   wherein the chiral amine is selected from the group consisting of: (S)—N-Benzyl-alpha-methylbenzylamine, (1R,2R)-2-Amino-1-phenyl-1,3-propanediol, (R)-1-(1-Naphthyl)ethylamine, (S)-2-Amino-3-phenyl-1-propanol, and L-Phenylalaninamide, and
   wherein the solvent is selected from the group consisting of: $C_5$-$C_{10}$ aliphatic hydrocarbons, aromatic hydrocarbons, $C_1$-$C_6$ alcohols, $C_2$-$C_8$ ethers, $C_2$-$C_8$ esters, $C_3$-$C_8$ ketones, nitriles, water, and a mixture of two or more thereof.

2. The method according to claim 1, wherein the substituted 2-trifluoromethyl-2H-chromene-3-carboxylic acid is represented by the following formula I:

wherein $R^1$ is one or more independently selected from the group consisting of halogen, $C_1$-$C_6$-alkyl, deutero-$C_1$-$C_6$-alkyl, $C_2$-$C_6$-alkenyl, deutero-$C_2$-$C_6$-alkenyl, $C_2$-$C_6$-alkynyl, deutero-$C_2$-$C_6$-alkynyl, $C_1$-$C_6$-alkoxy, deutero-$C_1$-$C_6$-alkoxy, $C_3$-$C_6$-cycloalkyl, $C_1$-$C_6$-alkoxy-$C_1$-$C_6$-alkyl, $C_1$-$C_6$-haloalkyl, $C_1$-$C_6$-haloalkoxy, and cyano.

3. The method according to claim 1, wherein the substituted 2-trifluoromethyl-2H-chromene-3-carboxylic acid is selected from the group consisting of:
   6-chloro-7-tert-butyl-2-trifluoromethyl-2H-chromene-3-carboxylic acid,
   6-chloro-8-methyl-2-trifluoromethyl-2H-chromene-3-carboxylic acid,
   6-chloro-8-ethyl-2-trifluoromethyl-2H-chromene-3-carboxylic acid,
   6-chloro-5,7-dimethyl-2-trifluoromethyl-2H-chromene-3-carboxylic acid,
   6,8-dimethyl-2-trifluoromethyl-2H-chromene-3-carboxylic acid,
   6,8-dichloro-2-trifluoromethyl-2H-chromene-3-carboxylic acid,
   8-ethyl-6-trifluoromethoxy-2-trifluoromethyl-2H-chromene-3-carboxylic acid,
   6-bromo-8-methyl-2-trifluoromethyl-2H-chromene-3-carboxylic acid, and
   6-bromo-8-(methyl-D3)-2-trifluoromethyl-2H-chromene-3-carboxylic acid.

4. The method according to claim 1, wherein the substituted 2-trifluoromethyl-2H-chromene-3-carboxylic acid is 6-chloro-7-tert-butyl-2-trifluoromethyl-2H-chromene-3-carboxylic acid.

5. The method according to claim 1, wherein the temperature of the transformation mixture is in the range of from 30° C. to 160° C.

6. The method according to claim 1, wherein the UV light irradiation is carried out by the UV light having a wavelength from 210 nm to 150 nm.

7. The method according to claim 1, wherein the UV light irradiation is carried out by the UV light having a wavelength from 330 nm to 390 nm.

8. The method according to claim 1, wherein the solubility of the salt of the undesired enantiomer is 1.2 times or more than the salt of the desired enantiomer.

* * * * *

UNITED STATES PATENT AND TRADEMARK OFFICE
CERTIFICATE OF CORRECTION

| | | |
|---|---|---|
| PATENT NO. | : 11,555,023 B2 | Page 1 of 1 |
| APPLICATION NO. | : 17/423280 | |
| DATED | : January 17, 2023 | |
| INVENTOR(S) | : Yoshiyuki Okumura et al. | |

It is certified that error appears in the above-identified patent and that said Letters Patent is hereby corrected as shown below:

In the Claims

Claim 5, Column 28, Line 46, "30° C." should be deleted and -- −30° C. -- should be added.

Claim 6, Column 28, Line 49, "150 nm" should be deleted and -- 450 nm -- should be added.

Signed and Sealed this
Twenty-first Day of March, 2023

Katherine Kelly Vidal
*Director of the United States Patent and Trademark Office*